United States Patent [19]

Didier et al.

[11] Patent Number: 5,681,970

[45] Date of Patent: Oct. 28, 1997

[54] METHOD FOR THE PREPARATION OF β-PHENYLISOSERINE DERIVATIVES

[75] Inventors: Eric Didier, Paris; Patrick Leon, Tassin-la-Demi-Lune, both of France

[73] Assignee: Rhone-Poulenc Rorer S.A., Antony, France

[21] Appl. No.: 525,786

[22] PCT Filed: Mar. 25, 1994

[86] PCT No.: PCT/FR94/00339

§ 371 Date: Sep. 28, 1995

§ 102(e) Date: Sep. 28, 1995

[87] PCT Pub. No.: WO94/22813

PCT Pub. Date: Oct. 13, 1994

[30] Foreign Application Priority Data

Mar. 29, 1993 [FR] France ................... 93 03575

[51] Int. Cl.⁶ .................................. C07D 305/14
[52] U.S. Cl. .................................. 549/510; 549/511
[58] Field of Search .................. 549/510, 511; 560/23, 463, 470

[56] References Cited

FOREIGN PATENT DOCUMENTS 0414610  2/1991  European Pat. Off. .

OTHER PUBLICATIONS

Palomo et al., Highly Stereoselective Synthesis of α-Hydroxy β-Amino acids through β-Lactams:Application to the Synthesis of the Taxol and Bestatin Side Chains and Related Systems, Tetrahedron Letters, vol. 31, (44): 6429–6432, (1990).

Furukawa et al. A Steroselective Synthesis of α–Chloro–α–phenylacetamide by the Reaction of Optically Active Schiff Base with Dichlorocarbene, Chem. Pharm. Bull., 25, 181–184 (1977).

Denis et al., An Efficient, Enantioselective Synthesis of the Taxol Side Chain, J. Org. Chem., 51:46–50 (1986).

Primary Examiner—Ba K. Trinh
Attorney, Agent, or Firm—Finnegan, Henderson, Farabow, Garrett & Dunner, L.L.P.

[57] ABSTRACT

Method for the preparation of β-phenylisoserine derivatives of general formula (I) involving the action of an anhydride and hydrogen with a product of general formula (II). The products of general formula (I) are especially useful in the preparation of taxoids having outstanding antitumour properties. In general formulae (I) and (II), Ar is an aryl radical, Ph is a phenyl radical or an optionally substituted α or β-naphtyl. R is a hydrogen atom or an alkyl radical optionally substituted by a phenyl radical and $R_1$ is an optionally substituted phenyl radical or a $R_2$—O radical wherein $R_2$ is an alkyl, alkenyl, cycloalkyl, phenyl or heterocyclyl.

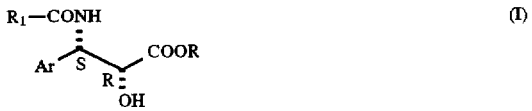

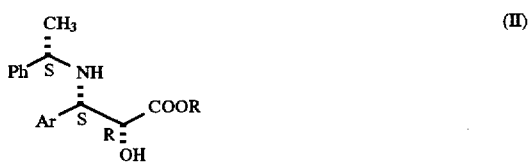

15 Claims, No Drawings

METHOD FOR THE PREPARATION OF β-PHENYLISOSERINE DERIVATIVES

This application is a 371 of PCT/FR94/00339 dated Mar. 25, 1994.

The present invention relates to a process for the preparation of α-phenylisoserine derivatives of general formula:

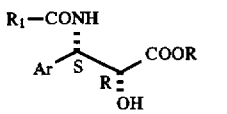  (I)

in which:

Ar represents an aryl radical and R represents a hydrogen atom or an alkyl radical optionally substituted with a phenyl radical and R₁ represents a phenyl radical optionally substituted with one or more atoms or radicals, which may be identical or different, chosen from halogen atoms and alkyl, hydroxyl, alkoxy, alkanoyl, alkanoyloxy, nitro, amino, alkylamino, dialkylamino, carbamoyl and trifluoromethyl radicals, the alkyl radicals and the alkyl portions of the other radicals containing 1 to 4 carbon atoms, or alternatively R₁ represents a radical R₂—O— in which R₂ represents:

- a straight or branched alkyl radical containing 1 to 8 carbon atoms, an alkenyl radical containing 3 to 6 carbon atoms, a cycloalkyl radical containing 3 to 6 carbon atoms or a cycloalkenyl radical containing 4 to 6 carbon atoms, these radicals being optionally substituted with one or more substitutents chosen from halogen atoms and hydroxyl radicals, alkyloxy radicals containing 1 to 4 carbon atoms, dialkylamino radicals in which each alkyl portion contains 1 to 4 carbon atoms, piperidino and morpholino radicals, 1-piperazinyl radicals (optionally substituted in the 4-position with an alkyl radical containing 1 to 4 carbon atoms or with a phenylalkyl radical in which the alkyl portion contains 1 to 4 carbon atoms), cycloalkyl radicals containing 4 to 6 carbon atoms, alkenyl radicals containing 4 to 6 carbon atoms, phenyl, cyano and carboxyl radicals, and alkyloxycarbonyl radicals in which the alkyl portion contains 1 to 4 carbon atoms,
- or a phenyl radical optionally substituted with one or more atoms or radicals chosen from halogen atoms and alkyl radicals containing 1 to 4 carbon atoms, and alkyloxy radicals containing 1 to 4 carbon atoms,
- or a saturated or unsaturated 5- or 6-membered nitrogen-containing heterocyclic radical optionally substituted with one or more alkyl radicals containing 1 to 4 carbon atoms.

Ar preferably represents a phenyl or α- or β-naphthyl radical optionally substituted with one or more atoms or radicals chosen from halogen atoms (fluorine, chlorine, bromine and iodine) and alkyl, aryl, aralkyl, alkoxy, alkylthio, aryloxy, arylthio, hydroxyl, hydroxyalkyl, mercapto, formyl, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, it being understood that the alkyl radicals and the alkyl portions of the other radicals contain 1 to 4 carbon atoms and that the aryl radicals are phenyl or α- or β-naphthyl radicals.

More particularly, Ar represents a phenyl radical optionally substituted with one or more atoms or radicals, which may be identical or different, chosen from halogen atoms and alkyl, alkoxy, amino, alkylamino, dialkylamino, acylamino, alkoxycarbonylamino and trifluoromethyl radicals.

Even more particularly, Ar represents a phenyl radical optionally substituted with a chlorine or fluorine atom or with an alkyl (methyl), alkoxy (methoxy), dialkylamino (dimethylamino) or acylamino (acetylamino) radical.

According to the present invention, the products of general formula (I) are obtained by the action of an anhydride of general formula:

$(R_1-CO)_2O$  (II)

in which R₁ is defined as above, in the presence of hydrogen, on a product of general formula:

  (III)

in which Ar and R are as defined above and Ph represents a phenyl or α- or β-naphthyl radical optionally substituted with one or more atoms or radicals chosen from halogen atoms (fluorine, chlorine, bromine and iodine) and alkoxy radicals containing 1 to 4 carbon atoms, alkylthio radicals containing 1 to 4 carbon atoms, dialkylamino radicals in which each alkyl portion contains 1 to 4 carbon atoms, and nitro radicals. More particularly, Ph represents a phenyl radical optionally substituted with one or more radicals, which may be identical or different, chosen from methoxy, methylthio, methylamino, dimethylamino and nitro radicals.

The process is generally carried out by reacting the anhydride of general formula (II) in the presence of hydrogen, optionally under pressure, and in the presence of a hydrogenolysis catalyst, with the product of general formula (III), in an organic solvent at a temperature between 0° C. and the reflux temperature of the reaction mixture.

The hydrogen required to carry out the process may optionally be provided by a compound which releases hydrogen by chemical reaction or by thermal decomposition, such as ammonium formate.

According to a preferred embodiment of the process, it is performed at a hydrogen pressure which may be between 1 and 50 bar.

The catalyst preferably consists of palladium-on-charcoal containing from 1 to 10% by weight of palladium or palladium dihydroxide-on-charcoal containing up to 10% by weight of palladium.

The process is carried out in an organic solvent or in a mixture of organic solvents.

As organic solvents which are particularly suitable, there may be mentioned aliphatic alcohols containing 1 to 4 carbon atoms, such as methanol, ethanol or isopropanol, aliphatic acids such as acetic acid, and aromatic hydrocarbons such as benzene, toluene or xylenes.

The process is preferably carried out in an aliphatic alcohol containing 1 to 4 carbon atoms, and more particularly in methanol, or in an aromatic hydrocarbon, and more particularly in toluene.

The process according to the invention may also be carried out by passing via an intermediate product of general formula:

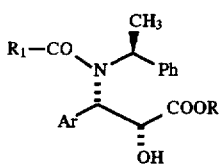

in which Ar, R, R₁ and Ph are defined as above, which product is hydrogenolysed into a product of general formula (I).

The product of general formula (IV) is generally obtained by the action of the anhydride of general formula (II) on the product of general formula (III) in the absence of hydrogen and of hydrogenation catalyst, preferably working in an aromatic hydrocarbon.

Hydrogenolysis of the product of general formula (IV) is generally carried out using hydrogen in the presence of a catalyst as defined above, preferably working in an aliphatic alcohol containing 1 to 4 carbon atoms, such as methanol.

It is not necessary to isolate the product of general formula (IV) prior to performing the hydrogenolysis.

The product of general formula (III) may be obtained by hydrolysis or alcoholysis of a product of general formula:

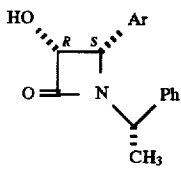

in which Ar and Ph are defined as above.

It is particularly advantageous to carry out an alcoholysis using an alcohol of general formula R-OH in which R is defined as above, working in acidic medium.

The alcoholysis is preferably carried out using methanol in the presence of a strong inorganic acid such as hydrochloric acid.

It is advantageous to carry out the alcoholysis at a temperature in the region of the reflux temperature of the reaction mixture.

The product of general formula (V) may be obtained by saponification or hydrogenolysis of a product of general formula:

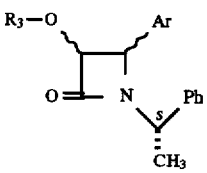

in which Ar and Ph are defined as above and R₃ represents a group which protects the alcohol function in ester or ether form, followed by separation of the 3R,4S diastereoisomer of general formula (IV) from the other diastereoisomers.

More particularly, R₃ represents an alkyl, phenylalkyl or phenyl radical or a radical R'₃—CO in which R'₃ represents an alkyl, phenylalkyl or phenyl radical.

Generally, when the alcohol function is protected in ester form, a saponification is carried out using an inorganic or organic base such as aqueous ammonia, lithium hydroxide, sodium hydroxide or potassium hydroxide, in a suitable solvent.

An aqueous-organic medium such as a methanol/water or tetrahydrofuran/water mixture is preferably used as solvent. The reaction is carried out at a temperature between $-10°$ and $+20°$ C.

Generally, when the alcohol function is protected in ether form, a hydrogenolysis is carried out using hydrogen, optionally generated in situ, for example by decomposition of ammonium formate, in the presence of a catalyst such as palladium-on-charcoal containing from 1 to 10% of palladium (w/w).

The separation of the (3R,4S) diastereoisomer may be carried out by selective crystallization in a suitable organic solvent such as ethyl acetate, optionally in the presence of an aliphatic hydrocarbon such as hexane, or by chromatography on silica.

The product of general formula (VI) may be obtained by cycloaddition of an imine of general formula:

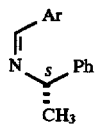

in which Ar and Ph are defined as above, to an acid halide of general formula:

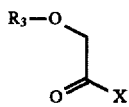

in which R₃ is defined as above and X represents a halogen atom such as a bromine or chlorine atom.

The reaction is generally carried out at a temperature between $-20°$ and $50°$ C., preferably in the region of $0°$ C., in the presence of a base chosen from tertiary amines (triethylamine and N-methylmorpholine) and pyridine, in an organic solvent chosen from optionally halogenated aliphatic hydrocarbons such as methylene chloride or chloroform, and aromatic hydrocarbons such as benzene, toluene or xylenes.

The product of general formula (V) may be obtained under the conditions described by M. Furukawa et al., Chem. Pharm. Bull., 25(1), 181–184 (1977).

The product of general formula (I) in which R represents a hydrogen atom may also be obtained by saponification of a product of general formula (I) in which R represents an alkyl radical containing 1 to 4 carbon atoms, optionally substituted with a phenyl radical, or represents a phenyl radical.

The saponification is generally performed using an inorganic base such as an alkali metal hydroxide (lithium hydroxide or sodium hydroxide) or an alkali metal carbonate or bicarbonate (sodium bicarbonate or potassium carbonate), in an aqueous-alcoholic medium such as a methanol/water mixture, working at a temperature between $10°$ and $40°$ C., preferably in the region of $25°$ C.

The products of general formula (I) are particularly useful for preparing the taxane derivatives of general formula:

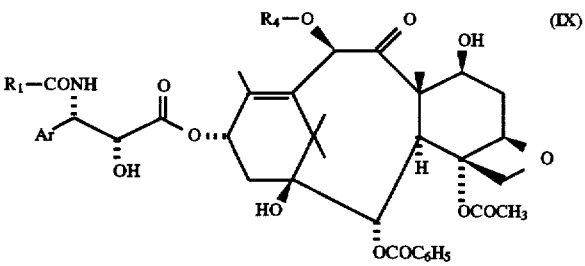

in which Ar and R₁ are defined as above and R₄ represents a hydrogen atom or an acetyl radical, these derivatives displaying remarkable antitumour and antileukaemia properties.

The product of general formula (IX) in which Ar represents a phenyl radical, R₁ represents a phenyl radical and R₄ represents an acetyl radical, is known by the name of Taxol, and that for which Ar represents a phenyl radical, R₁ represents a tert-butoxy radical and R₄ represents a hydrogen atom is known by the name of Taxotère.

The taxane derivatives of general formula (IX) may be obtained by the action of an acid of general formula:

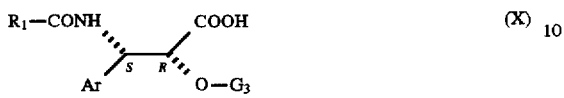
(X)

in which Ar and R₃ are defined as above and G₃ represents a protecting group for the hydroxyl function such as a methoxymethyl, (1-ethoxy) ethyl, benzyloxymethyl, (β-trimethylsilylethoxy)methyl, tetrahydropyranyl, 2,2,2-trichloroethoxymethyl or 2,2,2-trichloroethoxycarbonyl radical, optionally in halide, anhydride or mixed anhydride form, on a taxane derivative of general formula:

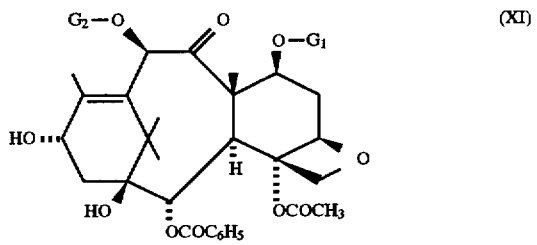
(XI)

in which G₁ represents a protecting group for the hydroxyl function such as a 2,2,2-trichloroethoxycarbonyl, trialkylsilyl, dialkylarylsilyl, alkyldiarylsilyl or triarylsilyl radical in which each alkyl part contains 1 to 4 carbon atoms and each aryl portion preferably represents a phenyl radical, and G₂ represents an acetyl radical or a protecting group for the hydroxyl function such as a 2,2,2-trichloroethoxycarbonyl radical, to give a product of general formula:

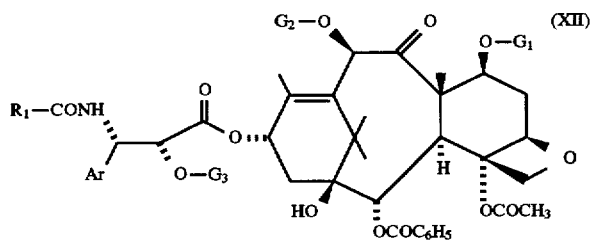
(XII)

in which Ar, R₁, G₁, G₂ and G₃ are defined as above, followed by replacement of the groups G₁, G₂ and G₃ by hydrogen atoms.

The esterification is generally carried out in the presence of a coupling agent such as a carbodiimide, for instance dicyclohexylcarbodiimide, or a reactive carbonate, for instance 2-pyridyl carbonate, and an activating agent such as an aminopyridine, for instance 4-dimethylaminopyridine or 4-pyrrolidinopyridine, working in an organic solvent such as an aromatic hydrocarbon (benzene, toluene, xylene, ethylbenzene, isopropylbenzene or chlorobenzene), an ether (tetrahydrofuran), a nitrile (acetonitrile) or an ester (ethyl acetate), at a temperature between 0° and 90° C.

Replacement of the protecting groups G₁, G₂ and G₃ by hydrogen atoms is generally carried out by treatment with zinc in the presence of acetic acid at a temperature between 30° and 60° C., or using an inorganic or organic acid such as hydrochloric acid or acetic acid in solution in an aliphatic alcohol containing 1 to 3 carbon atoms in the presence of zinc, when one of the protecting groups represents a 2,2,2-trichloroethoxycarbonyl radical, or by treatment in acidic medium when one of the protecting groups represents a silyl radical.

The acid of general formula (X) may be obtained by saponification of an ester of general formula:

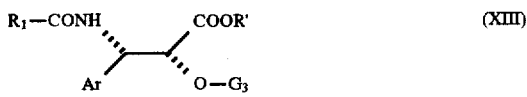
(XIII)

in which Ar, R₁ and G₃ are defined as above and R' represents an alkyl radical containing 1 to 4 carbon atoms, optionally substituted with a phenyl radical, or represents a phenyl radical, using an inorganic base such as an alkali metal hydroxide (lithium hydroxide or sodium hydroxide) or an alkali metal carbonate or bicarbonate (sodium bicarbonate or potassium carbonate), in aqueousalcoholic medium such as a methanol/water mixture, working at a temperature between 10° and 40° C., preferably in the region of 25° C.

The product of general formula (XIII) may be obtained under the usual conditions for the preparation of ethers, and more particularly according to the processes described by J-N. Denis et al., J. Org. Chem., 51, 46–50 (1986), starting with a product of general formula (I) in which R represents an alkyl radical containing 1 to 4 carbon atoms optionally substituted with a phenyl radical.

The taxane derivatives of general formula (IX) may also be obtained by first converting a product of general formula (I), in which R represents a hydrogen atom, into an oxazolidine derivative of general formula:

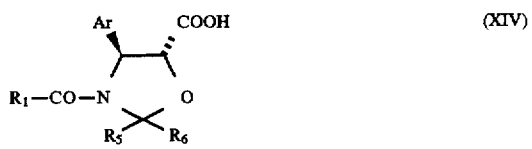
(XIV)

in which Ar and R₁ are defined as above and R₅ and R₆, which may be identical or different, represent a hydrogen atom or an alkyl radical containing 1 to 4 carbon atoms or an aryl radical, preferably a phenyl radical optionally substituted with one or more alkoxy radicals containing 1 to 4 carbon atoms, or alternatively R₅ represents an alkoxy radical containing 1 to 4 carbon atoms or a trihalomethyl radical such as trichloromethyl and R₆ represents a hydrogen atom, or alternatively R₅ and R₆ together with the carbon atom to which they are attached, form a 4- to 7-membered ring, and then by esterifying the taxane derivative of general formula (XI) using the acid of general formula (XIV), in order to obtain a product of general formula:

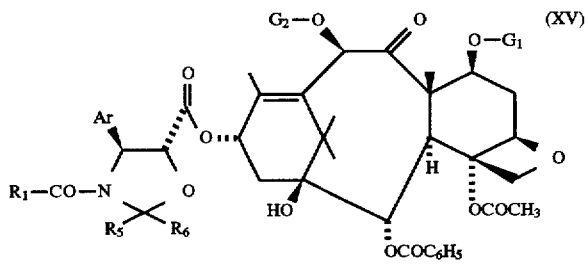
(XV)

in which Ar, G₁, G₂, R₁, R₅ and R₆ are defined as above, which product is converted into a taxane derivative of general formula (IX) by passing, when R₅ and R₆, which may be identical or different, represent an alkyl radical containing 1 to 4 carbon atoms or an aryl radical, preferably an optionally substituted phenyl radical, or alternatively $R_5$ represents a trihalomethyl radical or a phenyl radical substituted with a trihalomethyl radical and $R_6$ represents a hydrogen atom, or alternatively $R_5$ and $R_6$, together with the carbon atom to which they are attached, form a 4- to 7-membered ring, via an intermediate taxane derivative of general formula:

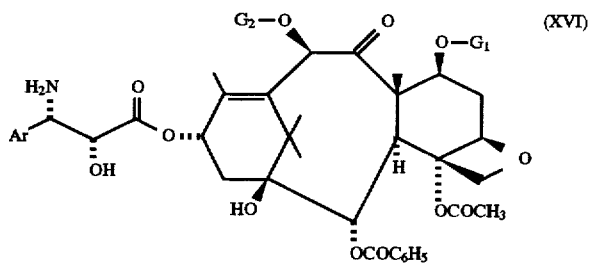

which is acylated using benzoyl chloride or using a product of general formula:

in which $R_1$ is defined as above and X represents a halogen atom (fluorine or chlorine), working, for example, under the conditions described in PCT Application WO 92/09589, before obtaining a product of general formula:

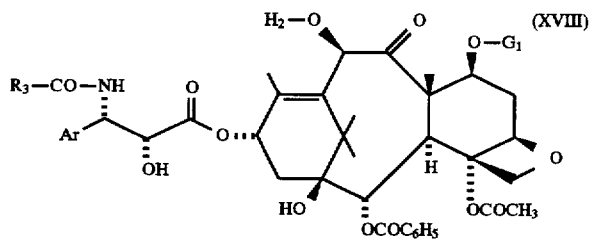

in which the protecting groups $G_1$ and $G_2$ are replaced by hydrogen atoms under the conditions described above.

The examples which follow illustrate the invention.

EXAMPLE 1

To a solution of 250 g of methyl (2R,3S)-2-hydroxy-3-[1-(S)-phenyl]ethylamino-3-phenylpropionate in 1000 cm³ of methanol is added, at 25° C., a solution of 198 g of di-tert-butyl dicarbonate in 250 cm³ of methanol and 50 g of 10% palladium-on-charcoal (50% water). The solution is then hydrogenated at atmospheric pressure of hydrogen at 25° C. for 10 hours. The catalyst is filtered off on sintered glass covered with Clarcel, and is washed twice with 110 cm³ of methanol. The filtrate and the washings are combined and cooled to 0° C. 510 cm³ of demineralized water are then added over one hour forty minutes. The solution is filtered on sintered glass and the product washed twice with 200 cm³ of a methanol/water mixture (70/30 by volume). After drying, 182.5 g of methyl (2R,3S)-3-tert-butoxycarbonylamino-2-hydroxy-3-phenylpropionate are obtained, melting at 135° C. (after recrystallization from diisopropyl ether) and the characteristics of which are as follows:

optical rotation:
$[\alpha]_D^{20}$=−2.6° (c=1; methanol)
$[\alpha]_D^{20}$=−7.4° (c=1.03; chloroform)

NMR spectrum (200 MHz; CDCl₃; chemical shifts δ in ppm; coupling constants J in Hz): 1.42 (s, 3H: —NH— COOC(CH₃)₃); 3.16 (d, 1H, J=5: —O$\underline{H}$); 3.87 (s, 3H: COOC$\underline{H}_3$); 4.48 (m, 1H: —C$\underline{H}$OH); 5.22 (broad d, 1H, J=10.5: —C$\underline{H}$NHCOOC(CH₃)₃); 5.39 (d, 1H, J=10.5: —N$\underline{H}$COOC (CH₃)₃); 7.20 to 7.45 (m,5H: —C₆H₅).

Methyl (2R, 3S)-2-hydroxy-3-[1-(S)-phenyl]ethylamino-3-phenylpropionate may be prepared in the following way:

A solution of 0.8 g of (3R,4S)-3-hydroxy-4-phenyl-1-[1-(S)-phenyl]ethyl-2-azetidinone in a mixture of 30 cm³ of methanol and 6 cm³ of aqueous 6N hydrochloric acid solution is heated at reflux (65° C.) for 20 hours, and then cooled to a temperature in the region of 20° C. and concentrated to dryness under reduced pressure (2.7 kPa) at a temperature in the region of 40° C. 20 cm³ of distilled water are added to the residue, and this is basified to a pH in the region of 7 by addition of aqueous 7.5N sodiumhydroxide solution and then extracted with 3 times 25 cm³ of dichloromethane. The organic phases are combined, dried over magnesium sulphate, filtered and then concentrated to dryness under reduced pressure (2.7 kPa) at 40° C. 0.74 g of methyl (2R,3S)-2-hydroxy-3-[1-(S)-phenyl]ethylamino-3-phenylpropionate is thus obtained in the form of a pale yellow oil, the characteristics of which are as follows:

optical rotation: $[\alpha]_D^{20}$=22.7° (c=1.00; methanol)

NMR spectrum (200 MHz; CDCl₃) δ (ppm): 1.34 (d, 3H, J=7 Hz: —CC$\underline{H}_3$); 2.7 (m, 2H: —CN$\underline{H}$C— and —O $\underline{H}$); 3.71 (q,) 1H, J=7 Hz: —C$\underline{H}$NH—); 3.84 (s, 3H: —COOC$\underline{H}_3$); 4.2 (d, 1H, J=4 Hz: —C$\underline{H}$OH—); 4.35 (d, 1H, J=4 Hz: —C$\underline{H}$NH—); 7.20 to 7.45 (m, 5H: —C₆H₅).

(3R 4S) -3-Hydroxy-4-phenyl-1-[1-(S)-phenyl]ethyl-2-azetidinone may be prepared according to one of the following methods:

1) To a mixture of 120 cm³ of aqueous 1N potassium hydroxide solution and 90 cm³ of tetrahydrofuran is added over 35 minutes, with stirring and at a temperature in the region of 0° C., a solution of 3.3 g of a mixture in a 75/25 molar proportion of the two diastereoisomers of 3-acetoxy-4-phenyl-1-[1-(S)-phenyl]ethyl-2-azetidinone, A form and B form, in 120 cm³ of tetrahydrofuran. Once the addition is complete, the reaction medium is stirred at a temperature in the region of 0° C. for one hour, followed by addition of 120 cm³ of saturated aqueous sodium hydrogen carbonate solution and 100 cm³ of distilled water. The aqueous phase is separated out after settling and is reextracted with 3 times 100 cm³ of ethyl acetate. The organic phases are combined, dried over magnesium sulphate, filtered and then concentrated to dryness under reduced pressure (2.7 kPa) at 40° C. 2.8 g of white crystals are thus obtained, which product is recrystallized from 35 cm³ of a mixture of ethyl acetate and hexane (80/20 by volume) to give 1.92 g of (3R,4S)-3-hydroxy-4-phenyl-1-[1-(S)-phenyl]ethyl-2-azetidinone in the form of white crystals melting at 162° C., the characteristics of which are as follows:

optical rotation: $[\alpha]_D^{20}$=+132° (c=1.08; methanol)

NMR spectrum (200 MHz; CDCl₃) δ (ppm): 1.41 (d, 3H, J=7 Hz: —CHC$\underline{H}_3$); 2.36 (d, 1H, J=8.5 Hz: —O$\underline{H}$); 4.58 (d, 1H, J=4.5 Hz: —C$\underline{H}$C₆H₅); 4.90 (dd, 1H, J=8.5 Hz and 4.5 Hz: —C$\underline{H}$OH—); 5.06 (q, 1H, J=7 Hz: —C $\underline{H}$CH₃); 7.20 to 7.50 (m, 5H: —C₆H₅).

The mixture of the A form and the B form of 3-acetoxy-4-phenyl-1-[1-(S)-phenyl]ethyl-2-azetidinone may be prepared in the following way:

To a solution of 14.63 g of (S)-N-benzylidene-(1-phenylethylamine) in 180 cm³ of chloroform are added, with stirring and at a temperature in the region of 20° C., 19.6 cm³ of triethylamine, followed by cooling of the reaction mixture to a temperature in the region of −20° C. and dropwise addition, over 75 minutes and while maintaining this temperature, of 5.17 cm³ of 2-acetoxyacetyl chloride in 90 cm³ of chloroform. The solution obtained is stirred for 16 hours at a temperature in the region of 20° C., followed by addition of 300 cm³ of aqueous 2.7N hydrochloric acid solution. The organic phase is separated out after settling, washed with twice 300 cm³ of distilled water and then with 300 cm³ of saturated aqueous sodium hydrogen carbonate solution, dried over magnesium sulphate, filtered and then concentrated to dryness under reduced pressure (2.7 kPa) at 40° C. 16.5 g of a brown oil are thus obtained, which product is purified by chromatography on 800 g of silica (0.04-0.063 mm) contained in a column 6.8 cm in diameter [eluent: cyclohexane/ethyl acetate (70/30 by volume)], collecting 22 cm³ fractions. Fractions 100 to 153 are combined and concentrated to dryness under reduced pressure (0.27 kPa) at 40° C. 10.65 g of a mixture in a 75/25 molar proportion of two diastereoisomers of 3-acetoxy-4-phenyl-1-[1-(S)-phenyl]ethyl-2-azetidinone are thus obtained in the form of a yellow oil.

(S)-N-Benzylidene-(1-phenylethylamine) may be prepared according to the method described by M. Furukawa et al., Chem. Pharm. Bull., 1977, 25(1), 181–184.

2) Working as above, but starting with 100 mg of a mixture in a 70/30 molar proportion of the two diastereoisomers of 3-isobutyryloxy-4-phenyl-1-[1-(S)-phenylethyl-2azetidinone A form and B form, 82 mg of (3R,4S)-3-hydroxy-4-phenyl-1-[1-(S)-phenyl]ethyl-2-azetidinone are obtained in the form of white crystals melting at 162° C., the physical characteristics of which are identical to those of the product obtained above.

The mixture of the A and B forms of 3-isobutyryl-oxy-4-phenyl-1-[1-(S)-phenyl]ethyl-2-azetidinone may be prepared by working as above, but starting with 1.91 g of (S)-N-benzylidene-(1-phenylethylamine) and 1 g of 2-isobutyryloxyacetyl chloride. 1.27 g of a mixture in a 70/30 molar proportion of two diastereoisomers of 3-isobutyryloxy-4-phenyl-1-[1-(S)-phenyl]ethyl-2-azetidinone are thus obtained in the form of a yellow oil.

2-Isobutyryloxyacetyl chloride may be prepared in the following way:

To a solution of 5 g of glycolic acid in 100 cm³ of dichloromethane, maintained under an argon atmosphere, are added, with stirring and at a temperature in the region of 20° C., 18 cm³ of triethylamine, followed by cooling of the reaction mixture to a temperature in the region of 5° C. and dropwise addition, over 30 minutes and while maintaining this temperature, of 13.8 cm³ of isobutyryl chloride. The solution obtained is stirred for 3 hours at a temperature in the region of 20° C. The precipitate formed is separated out by filtration and washed with twice 10 cm³ of dichloromethane. The combined filtrates are washed with 60 cm³ of saturated aqueous ammonium chloride solution and then with 30 cm³ of saturated aqueous sodium chloride solution, dried over magnesium sulphate, filtered and then concentrated to dryness under reduced pressure (2.7 kPa) at 40° C. 13 g of a yellow oil are thus obtained, to which oil are added 24 cm³ of sulphinyl chloride. The solution obtained is refluxed for 2.5 hours and then distilled under reduced pressure (0.07 kPa; 0.5 mmHg). 3.4 g of 2-isobutyryloxy-acetyl chloride are thus obtained in the form of a colourless liquid distilling at 45°–50° C. at a pressure of 0.07 kPa.

3) To 43 mg of a dispersion containing 10% palladium in charcoal powder is added a solution of 91 mg of a mixture in a 60/40 molar proportion of the two diastereoisomers of 3-benzyloxy-4-phenyl-1-[1-(S)-phenyl]ethyl-2-azetidinone, A form and B form, in 6 cm³ of methanol, followed by 32 mg of ammonium formate. The reaction mixture is maintained under an argon atmosphere with stirring for 72 hours at a temperature in the region of 20° C., followed by addition of 56 mg of the dispersion containing 10% palladium, and 128 mg of ammonium formate. The reaction mixture is maintained at the same temperature with stirring for 26 hours. The reaction mixture is then filtered on sintered glass packed with Celite. The sintered glass is washed with 3 times 5 cm³ of dichloromethane and the combined filtrates are then concentrated under reduced pressure (2.7 kPa) at a temperature in the region of 40° C. 70 mg of white crystals are thus obtained, which product is purified, in 10 mg fractions, by chromatography on silica gel deposited on a plate (1 mm thickness of gel; 20×20 cm plate). After location, by UV rays, of the zone corresponding to the desired product, this zone is scraped off and the silica is collected and then washed on sintered glass with 10 times 5 cm³ of dichloromethane and with 5 times 2 cm³ of methanol. The filtrates are combined and concentrated to dryness under reduced pressure (0.27 kPa) at 40° C. 28 mg of (3R,4S)-3-hydroxy-4-phenyl-1-[1-(S)-phenyl]ethyl-2-azetidinone are thus obtained in the form of white crystals melting at 162° C., the physical characteristics of which are identical to those of the product obtained above.

The mixture of the A and B forms of 3-benzyloxy-4-phenyl-1-[1-(S)-phenyl]ethyl-2-azetidinone may be prepared by working as above, but starting with 2.0 g of (S)-N-benzylidene-(1-phenylethylamine) and 1.38 g of 2-benzyloxyacetyl chloride. 1.25 g of a mixture in a 60/40 molar proportion of two diastereoisomers of 3-benzyloxy-4-phenyl-1-[1-(S)-phenyl]ethyl-2-azetidinone are thus obtained in the form of a yellow oil.

EXAMPLE 2

1 g of methyl (2R,3S)-2-hydroxy-3-[1-(S)-phenyl] ethylamino-3-phenylpropionate, 0.8 g of benzoic anhydride, 14 cm³ of toluene and 0.2 g of 10% (w/w) palladium-on-charcoal are introduced into a 25 cm³ round-bottomed flask. The flask is flushed with argon and then placed under a hydrogen atmosphere. The reaction mixture is stirred for 23 hours at 20° C. and then for 3 hours at 87° C. After cooling and separation of the catalyst by filtration on sintered glass, the toluene solution is neutralized using saturated sodium bicarbonate solution.

The organic layer is washed with 10 cm³ of water. After drying and concentrating to dryness under reduced pressure, the residue is taken up in 10 cm³ of acetone. After filtration on a Whatman filter and washing of the filter with 10 cm³ of acetone and 10 cm³ of dichloromethane, the organic phases are combined and then concentrated to dryness under reduced pressure. 0.8 g of a product is thus obtained, the proton nuclear magnetic resonance analysis of which shows that it contains 10% of methyl (2R,3S)-3-benzoylamino-2-hydroxy-3-phenyl-propionate and 86% of methyl (2R,3S)-3-(N-benzoyl-N-phenyl -1-(S)-ethyl) amino-2-hydroxy-3-phenylpropionate.

EXAMPLE 3

0.51 g of methyl (2R, 3S)-2-hydroxy-3-[1-(S)-phenyl] ethylamino-3-phenylpropionate, 0.39 g of benzoic anhydride and 7 cm³ of toluene are introduced into a 25 cm³ round-bottomed flask. The mixture is heated at 80° C. for 3 hours. The toluene is removed by distillation under reduced pressure. 7 cm³ of methanol and 0.128 g of 10% palladium-on-charcoal containing 50% water are then added. The mixture is heated at reflux for 3 hours 15 minutes. After cooling, the catalyst is separated out by filtration on sintered glass. The filtrate is rinsed with acetone. The organic phases are filtered on a Whatman filter and then concentrated to dryness under reduced pressure. The residue is taken up in 15 cm³ of an ethyl acetate/toluene mixture. The solution is washed with saturated sodium bicarbonate solution and then with twice 10 cm³ of water. After drying, filtration and concentration to dryness under reduced pressure, 0.4 g of a product is obtained, the proton nuclear magnetic resonance analysis of which shows that it contains 56% of methyl (2R,3S)-3-benzoylamino-2-hydroxy-3-phenyl-propionate and 33% of methyl (2R,3S)-3-[N-benzoyl-N-phenyl-1-(S)-ethyl]amino-2-hydroxy-3-phenylpropionate.

We claim:

1. A process for the preparation of β-phenyl-isoserine derivatives of the formula I:

in which Ar represents an aryl radical, R represents a hydrogen atom or an alkyl radical unsubstituted or substituted with a phenyl radical, and $R_1$ represents an unsubstituted or substituted phenyl radical or a radical $R_2$—O— in which $R_2$ represents a straight or branched alkyl radical containing 1 to 8 carbon atoms, an alkenyl radical containing 3 to 6 carbon atoms, a cycloalkyl radical containing 3 to 6 carbon atoms or a cycloalkenyl radical containing 4 to 6 carbon atoms, these radicals being unsubstituted or substituted with one or more substitutents chosen from halogen atoms and hydroxyl radicals, alkyloxy radicals containing 1 to 4 carbon atoms, dialkylamino radicals in which each alkyl portion contains 1 to 4 carbon atoms, piperidino and morpholino radicals, 1-piperazinyl radicals unsubstituted or substituted in the 4-position with an alkyl radical containing 1 to 4 carbon atoms or with a phenylalkyl radical in which the alkyl portion contains 1 to 4 carbon atoms, cycloalkyl radicals containing 4 to 6 carbon atoms, alkenyl radicals containing 4 to 6 carbon atoms, phenyl, cyano and carboxyl radicals and alkyloxycarbonyl radicals in which the alkyl portion contains 1 to 4 carbon atoms, or a phenyl radical unsubstituted or substituted with one or more atoms or radicals chosen from halogen atoms and alkyl radicals containing 1 to 4 carbon atoms, and alkyloxy radicals containing 1 to 4 carbon atoms, or a saturated or unsaturated 5- or 6-membered nitrogen-containing heterocyclic radical unsubstituted or substituted with one or more alkyl radicals containing 1 to 4 carbon atoms, comprising reacting an anhydride of the formula:

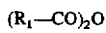

in which $R_1$ is defined as above, in the presence of hydrogen, with a product of the formula III:

in which Ar and R are defined as above and Ph represents a phenyl or α- or β-naphthyl radical unsubstituted or substituted with one or more atoms or radicals, which may be identical or different, selected from halogen atoms and alkoxy radicals containing 1 to 4 carbon atoms, alkylthio radicals containing 1 to 4 carbon atoms, dialkylamino radicals in which each alkyl portion contains 1 to 4 carbon atoms, and nitro radicals.

2. The process according to claim 1, wherein the reaction is performed in the presence of hydrogen and a catalyst.

3. The process according to claim 2, wherein the catalyst is selected from palladium-on-charcoal and palladium dihydroxide-on-charcoal.

4. The process according to claim 1, wherein the reaction is performed at a hydrogen pressure in the range of 1 to 50 bar.

5. The process according to claim 1, wherein the reaction is performed in an organic solvent selected from aliphatic alcohols containing 1 to 4 carbon atoms and aromatic hydrocarbons and mixtures thereof.

6. The process for the preparation of β-phenylisoserine derivatives of claim 1, wherein an anhydride of the formula:

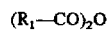

in which $R_1$ is defined as in claim 1, is reacted with a product of the formula III:

in which Ar, R and Ph are defined as in claim 1, to obtain a product of the formula IV:

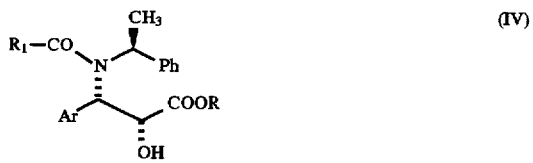

in which Ar, R, $R_1$, and Ph are defined as in claim 1, followed by hydrogenolysis of the product of formula IV using hydrogen in the presence of a catalyst hydrogenation.

7. The process according to claim 1, for the preparation of β-phenylisoserine derivatives of the formula I:

in which R and $R_1$ are defined as in claim 1, Ar represents a phenyl or α- or β-naphthyl radical optionally substituted with one or more atoms or radicals chosen from halogen atoms and alkyl, aryl, aralkyl, alkoxy, alkylthio, aryloxy, arylthio, hydroxyl, hydroxy-alkyl, mercapto, formyl, acylamino, aroylamino, alkoxycarbonyl-amino, amino, alkylamino, dialkylamino, carboxyl, alkoxycarbonyl, carbamoyl, dialkylcarbamoyl, cyano, nitro and trifluoromethyl radicals, wherein the alkyl radicals and the alkyl portions of the other radicals contain 1 to 4 carbon atoms and the aryl radicals are phenyl or α- or β-naphthyl radicals.

8. A method for preparing a taxane derivative of the formula (IX):

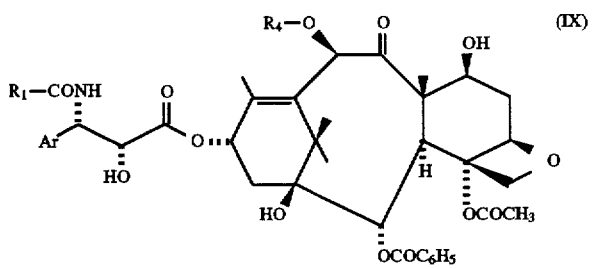

in which

Ar represents an aryl radical,

R₄ represents a hydrogen atom or an acetyl radical, and

R₁ represents a phenyl radical unsubstituted or substituted with at least one substituent, which may be identical or different, selected from a halogen atom and alkyl, hydroxyl, alkoxy, alkanoyl, alkanoyloxy, nitro, amino, alkylamino, dialkylamino, carbamoyl, and trifluoromethyl radicals, wherein the alkyl radicals and the alkyl portions of the other radicals comprise 1 to 4 carbon atoms, or a radical R₂—O— in which R₂ represents:

a straight or branched alkyl radical comprising 1 to 8 carbon atoms, an alkenyl radical comprising 3 to 6 carbon atoms, a cycloalkyl radical comprising 3 to 6 carbon atoms, or a cycloalkenyl radical comprising 4 to 6 carbon atoms, these radicals being unsubstituted or substituted with at least one substituent selected from a halogen atom, a hydroxyl radical, an alkyloxy radical comprising 1 to 4 carbon atoms, a dialkylamino radical in which each alkyl portion comprises 1 to 4 carbon atoms, a piperidino radical, a morpholino radical, a 1-piperazinyl radical (unsubstituted or substituted in the 4-position with an alkyl radical comprising 1 to 4 carbon atoms or with a phenylalkyl radical in which the alkyl portion comprises 1 to 4 carbon atoms), a cycloalkyl radical comprising 3 to 6 carbon atoms, an alkenyl radical comprising 4 to 6 carbon atoms, a phenyl radical, a cyano radical, a carboxyl radical, and an alkyloxycarbonyl radical in which the alkyl portion comprises 1 to 4 carbon atoms;

or a phenyl radical unsubstituted or substituted with at least one substituent selected from a halogen atom, an alkyl radical comprising 1 to 4 carbon atoms, and an alkyloxy radical comprising 1 to 4 carbon atoms;

or a saturated or unsaturated 4- to 6-membered nitrogen-comprising heterocyclic radical unsubstituted or substituted with at least one alkyl radical comprising 1 to 4 carbon atoms;

the method comprising the steps of:

a) reacting an anhydride of the formula (II):

$$(R_1-CO)_2O \quad (II)$$

in which R₁ is defined as above, in the presence of hydrogen, with a compound of the formula (III):

in which Ar is defined as above, R represents a hydrogen atom or an alkyl radical unsubstituted or substituted with a phenyl radical, and Ph represents a phenyl or α- or β-naphthyl radical unsubstituted or substituted with at least one substituent, which may be identical or different, selected from a halogen atom and an alkoxy radical comprising 1 to 4 carbon atoms, an alkylthio radical comprising 1 to 4 carbon atoms, a dialkylamino radical in which each alkyl portion comprises 1 to 4 carbon atoms, and a nitro radical;

b) performing hydrogenolysis on the product of step (a) and then protecting the OH group with a protecting group G₃, wherein G₃ represents a methoxymethyl, (1-ethoxy)-ethyl, benzyloxymethyl, (β-trimethylsilylethoxy)methyl, tetrahydropyranyl, 2,2,2-trichloroethoxymethyl, or 2,2,2-trichloroethoxycarbonyl radical;

c) reacting the product of step (b), optionally in a halide, anhydride, or mixed anhydride form, with a taxane derivative of the formula (XI):

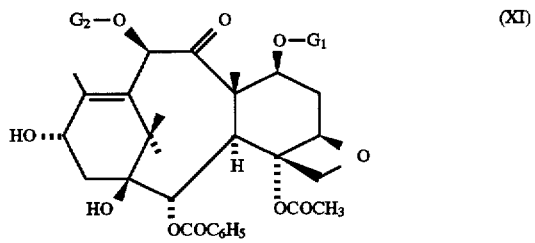

in which G₁ represents a protecting group for the hydroxyl function and G₂ represents an acetyl radical or a protecting group for the hydroxyl function; and d) replacing the protecting groups G₁, G₂, and G₃ by hydrogen.

9. A method for preparing a compound of formula (I):

in which Ar represents an aryl radical, R represents a hydrogen atom or an alkyl radical unsubstituted or substituted with a phenyl radical, and R₁ represents an unsubstituted or substituted phenyl radical or a radical R₂—O— in which R₂ represents:

a straight or branched alkyl radical comprising 1 to 8 carbon atoms, an alkenyl radical comprising 3 to 6 carbon atoms, a cycloalkyl radical comprising 3 to 6 carbon atoms, or a cycloalkenyl radical comprising 4 to 6 carbon atoms, these radicals being unsubstituted or substituted with at least one substituent selected from a halogen atom and a hydroxyl radical, an alkyloxy radical comprising 1 to 4 carbon atoms, a dialkylamino radical in which each alkyl portion comprises 1 to 4 carbon atoms, a piperidino radical, a morpholino radical, a 1-piperazinyl radical (unsubstituted or substituted in the 4-position with an alkyl radical comprising 1 to 4 carbon atoms or with a phenylalkyl radical in which the alkyl portion comprises 1 to 4 carbon atoms), a cycloalkyl radical comprising 4 to 6 carbon atoms, an alkenyl radical comprising 4 to 6 carbon atoms, a phenyl radical, a cyano radical, a carboxyl radical, and an alkyloxycarbonyl radical in which the alkyl portion comprises 1 to 4 carbon atoms;

or a phenyl radical unsubstituted or substituted with at least one substituent selected from a halogen atom, an alkyl radical comprising 1 to 4 carbon atoms, and an alkyloxy radical comprising 1 to 4 carbon atoms;

or a saturated or unsaturated 5- or 6-membered nitrogen-comprising heterocyclic radical unsubstituted or substituted with at least one alkyl radical comprising 1 to 4 carbon atoms;

the method comprising the steps of:

a) reacting a compound of the formula (VII):

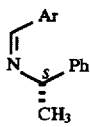
(VII)

in which Ar is defined as above and Ph represents a phenyl or α- or β-naphthyl radical unsubstituted or substituted with at least one substituent, which may be identical or different, selected from a halogen atom and an alkoxy radical comprising 1 to 4 carbon atoms, an alkylthio radical comprising 1 to 4 carbon atoms, a dialkylamino radical in which each alkyl portion comprises 1 to 4 carbon atoms, and a nitro radical, with an acid halide of the formula (VIII):

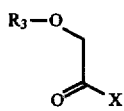
(VIII)

in which Ar and Ph are defined as above, $R_3$ represents an alkyl, phenylalkyl, or phenyl radical or a radical $R'_3$—CO in which $R'_3$ represents an alkyl, phenylalkyl, or phenyl radical, and X represents a halogen atom, to obtain a compound of formula (VI):

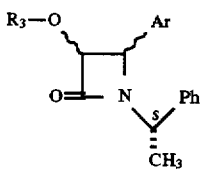
(VI)

b) saponifying or performing hydrogenolysis on the compound of formula (VI) to obtain a compound of the formula (V):

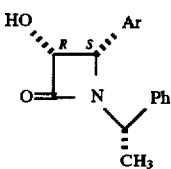
(V)

c) selectively crystallizing and then hydrolyzing or alcoholyzing the compound of formula (V) to obtain a compound of the formula (III):

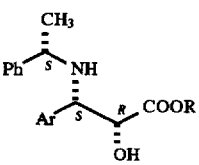
(III)

in which Ar, R, and Ph are defined as above; and d) reacting the compound of formula (III) with an anhydride of the formula (II)

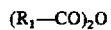
(II)

in which $R_1$ is defined as above, to obtain the compound of formula (I).

10. The method according to claim 8, wherein $G_1$ is a 2,2,2-trichloroethoxycarbonyl, trialkylsilyl, dialkylarylsilyl, alkyldiarylsilyl, or triarylsilyl radical in which each alkyl portion comprises 1 to 4 carbon atoms and each aryl portion represents a phenyl radical, and $G_2$ is a 2,2,2-trichloroethoxycarbonyl radical.

11. The method according to claim 8 wherein Ar represents a phenyl or α- or β-naphthyl radical unsubstituted or substituted with one or more atoms or radicals chosen from halogen atoms and alkyl, aryl, aralkyl, alkoxy, alkylthio, aryloxy, arylthio, hydroxyl, hydroxyalkyl, mercapto, formyl, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, wherein the alkyl radicals and the alkyl portions of the other radicals contain 1 to 4 carbon atoms and the aryl radicals are phenyl or α- or β-naphthyl radicals.

12. The method according to claim 11 wherein the halogen atoms are selected from the group consisting of fluorine, chlorine, bromine, and iodine.

13. A product of the formula IV:

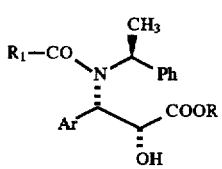
(IV)

wherein

Ar represents an aryl radical,

R represents a hydrogen atom or an alkyl radical unsubstituted or substituted with a phenyl radical, $R_1$ represents an unsubstituted or substituted phenyl radical or a radical $R_2$—O— in which $R_2$ represents a straight or branched alkyl radical containing 1 to 8 carbon atoms, an alkenyl radical containing 3 to 6 carbon atoms, a cycloalkyl radical containing 3 to 6 carbon atoms or a cycloalkenyl radical containing 4 to 6 carbon atoms, these radicals being unsubstituted or substituted with one or more substitutents chosen from halogen atoms and hydroxyl radicals, alkyloxy radicals containing 1 to 4 carbon atoms, dialkylamino radicals in which each alkyl portion contains 1 to 4 carbon atoms, piperidino and morpholino radicals, 1-piperazinyl radicals unsubstituted or substituted in the 4-position with an alkyl radical containing 1 to 4 carbon atoms or with a phenylalkyl radical in which the alkyl portion contains 1 to 4 carbon atoms, cycloalkyl radicals containing 3 to 6 carbon atoms, alkenyl radicals containing 4 to 6 carbon atoms, phenyl, cyano and carboxyl radicals and alkyloxycarbonyl radicals in which the alkyl portion contains 1 to 4 carbon atoms, a phenyl radical unsubstituted or substituted with one or more atoms or radicals chosen from halogen atoms and alkyl radicals containing 1 to 4 carbon atoms, and alkyloxy radicals containing 1 to 4 carbon atoms, or a saturated or unsaturated 4- or 6-membered nitrogen-containing heterocyclic radical unsubstituted or substituted with one or more alkyl radicals containing 1 to 4 carbon atoms, and Ph represents a phenyl or α- or β-naphthyl radical unsubstituted or substituted with one or more atoms or radicals, which may be identical or different, selected from halogen atoms and alkoxy radicals containing 1 to 4 carbon atoms, alkylthio radicals containing 1 to 4 carbon atoms, dialkylamino radicals in which each alkyl portion contains 1 to 4 carbon atoms, and nitro radicals.

14. A method of making the product of claim 13 by the reaction of an anhydride of the formula $(R_1—CO)_2O$, in which $R_1$ is defined as in claim 13, with a product of the formula III:
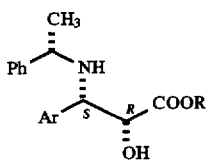 (III)
wherein Ar, Ph, and R as defined as in claim 13.
15. A method of using the product of claim 13 to prepare a β-phenylisoserine of the formula (I):
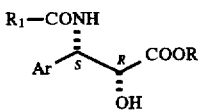 (I)
wherein Ar, R, and $R_1$ are defined as in claim 13, by hydrolyzing the product of claim 13 using hydrogen in the presence of a hydrogenation catalyst.
* * * * *

UNITED STATES PATENT AND TRADEMARK OFFICE
CERTIFICATE OF CORRECTION

PATENT NO. : 5,681,970
DATED : October 28, 1997
INVENTOR(S) : Eric Didier et al.

It is certified that error appears in the above-indentified patent and that said Letters Patent is hereby corrected as shown below:

Claim 1, column 11, line 14, "ß-phenyl-isoserine" should read --ß-phenylisoserine--;
  line 31, "substitutents" should read --substituents--.

Claim 6, column 12, line 46, "catalyst hydrogenation" should read --hydrogenation catalyst--.

Claim 8, in the formula (IX) at the top of column 13,

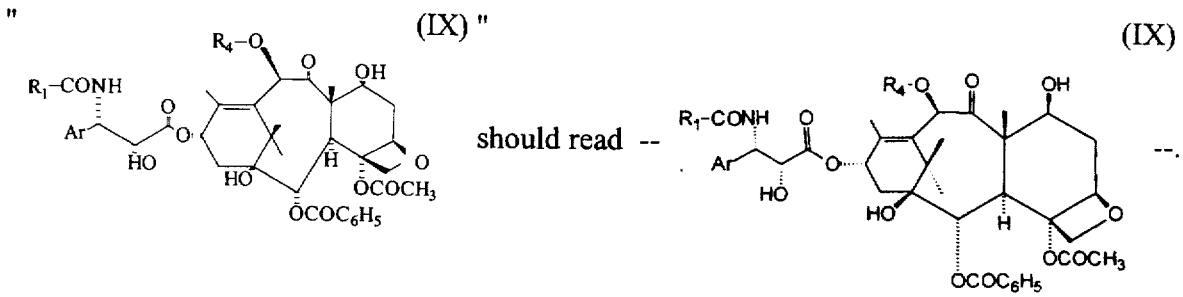

UNITED STATES PATENT AND TRADEMARK OFFICE
CERTIFICATE OF CORRECTION

PATENT NO. : 5,681,970
DATED : October 28, 1997
INVENTOR(S) : Eric Didier et al.

It is certified that error appears in the above-indentified patent and that said Letters Patent is hereby corrected as shown below:

Claim 13, column 16, line 38, "substitutents" should read --substituents--.

Signed and Sealed this

Eleventh Day of August 1998

Attest:

Attesting Officer

BRUCE LEHMAN

Commissioner of Patents and Trademarks